(12) United States Patent
Matsushita et al.

(10) Patent No.: US 9,713,581 B2
(45) Date of Patent: Jul. 25, 2017

(54) MAGNETIC POWDER FOR COSMETIC AGENT

(71) Applicant: MTG Co., Ltd., Nagoya-shi (JP)

(72) Inventors: Tsuyoshi Matsushita, Aichi (JP); Hiromichi Kobayashi, Chiba (JP)

(73) Assignee: MTG Co., Ltd., Nagoya-shi (JP)

( * ) Notice: Subject to any disclaimer, the term of this patent is extended or adjusted under 35 U.S.C. 154(b) by 0 days.

(21) Appl. No.: 14/774,373

(22) PCT Filed: Mar. 18, 2014

(86) PCT No.: PCT/JP2014/057247
§ 371 (c)(1),
(2) Date: Sep. 10, 2015

(87) PCT Pub. No.: WO2014/156804
PCT Pub. Date: Oct. 2, 2014

(65) Prior Publication Data
US 2016/0038383 A1     Feb. 11, 2016

(30) Foreign Application Priority Data

Mar. 29, 2013  (JP) ................. 2013-071151

(51) Int. Cl.
*B32B 5/16*     (2006.01)
*A61K 8/02*     (2006.01)
(Continued)

(52) U.S. Cl.
CPC ............ *A61K 8/022* (2013.01); *A61K 8/0225* (2013.01); *A61K 8/19* (2013.01); *A61Q 1/12* (2013.01);
(Continued)

(58) Field of Classification Search
CPC .......... A61K 8/02; A61K 8/0225; A61K 8/19; A61K 33/26; B22F 9/04; B22F 2301/35; B22F 2304/10
(Continued)

(56) References Cited

U.S. PATENT DOCUMENTS 3,695,934 A    10/1972  Feldhaus
4,046,591 A     9/1977  Laguerre
(Continued)

FOREIGN PATENT DOCUMENTS

CN    1826095 A    8/2006
CN    101305972 A   11/2008
(Continued)

OTHER PUBLICATIONS

International Search Report Issued May 13, 2014 in PCT/JP14/057247 Filed Mar. 18, 2014.
(Continued)

*Primary Examiner* — Holly Le
(74) *Attorney, Agent, or Firm* — Oblon, McClelland, Maier & Neustadt, L.L.P.

(57) ABSTRACT

A magnetic powder to be included in a cosmetic agent being removable by a magnetic attraction force from the cosmetic agent applied to the skin. The magnetic powder comprises a ferromagnetic ferrite, a mean volume particle diameter of 50 to 75 μm when determined from a particle size distribution obtained by a laser diffraction scattering method, a content of particles with a particle diameter of less than 37 μm of 15% by mass or less, and a content of particles with a particle diameter of 105 μm or more of 5% by mass or less. The magnetic powder preferably has a saturation magnetization of 80 $Am^2/kg$ or more.

6 Claims, 1 Drawing Sheet

(51) Int. Cl.
*B22F 9/04* (2006.01)
*A61Q 19/00* (2006.01)
*A61K 8/19* (2006.01)
*H01F 1/36* (2006.01)
*C01G 49/00* (2006.01)
*A61Q 1/12* (2006.01)
*C01G 49/08* (2006.01)

(52) U.S. Cl.
CPC ............... *A61Q 19/00* (2013.01); *B22F 9/04* (2013.01); *C01G 49/0072* (2013.01); *C01G 49/08* (2013.01); *H01F 1/36* (2013.01); *A61K 2800/412* (2013.01); *A61K 2800/47* (2013.01); *C01P 2004/61* (2013.01); *C01P 2006/10* (2013.01); *C01P 2006/12* (2013.01); *C01P 2006/42* (2013.01)

(58) Field of Classification Search
USPC ........................................................ 428/402
See application file for complete search history.

(56) References Cited

U.S. PATENT DOCUMENTS

| | | | |
|---|---|---|---|
| 5,419,994 A | 5/1995 | Honjo et al. | |
| 2005/0232955 A1 | 10/2005 | Maor et al. | |
| 2010/0003205 A1* | 1/2010 | Elliott | A61K 8/02 424/59 |

FOREIGN PATENT DOCUMENTS

| | | |
|---|---|---|
| DE | 36 34 121 A1 | 11/1987 |
| EP | 2 055 295 A2 | 5/2009 |
| JP | 61 3765 | 2/1986 |
| JP | 3 233464 | 10/1991 |
| JP | 3 280070 | 12/1991 |
| JP | 2004 155720 | 6/2004 |
| JP | 2004 187874 | 7/2004 |
| JP | 2004-224782 A | 8/2004 |
| JP | 2005 239563 | 9/2005 |

OTHER PUBLICATIONS

Supplementary European Search Report issued in Patent Application No. 14 774 259.7 issued Nov. 14, 2016.
Combined Chinese Office Action and Search Report issued Jul. 28, 2016 in Patent Application No. 201480014172.2 (with English Translation and English Translation of Categories of Cited Documents).
Taiwanese Office Action issued Mar. 29, 22017 in Taiwanese Patent Application No. 103111486 with English translation.
Chinese Office Action dispatched from the SIPO on Apr. 17, 2017 in Chinese Patent Application No. 201480014172.2 with English translation.

* cited by examiner

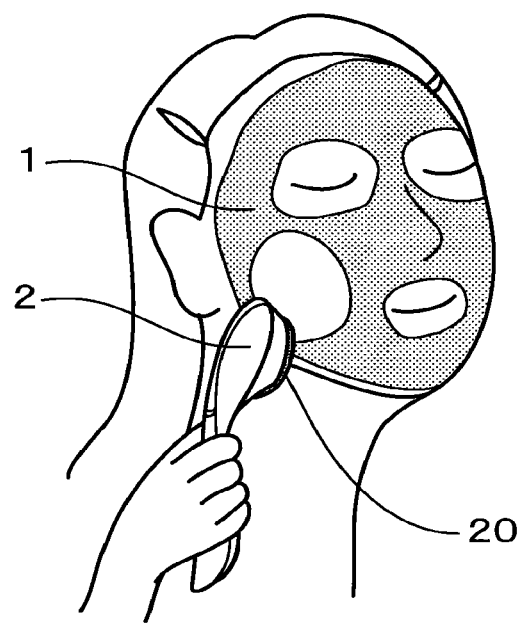

MAGNETIC POWDER FOR COSMETIC AGENT

TECHNICAL FIELD

The present invention relates to a magnetic powder to be included in a cosmetic agent applied to the skin.

BACKGROUND ART

As a paste-like cosmetic agent used for beautifying skin, a cosmetic agent has been known which is applied to skin and removed after a while, whereby impurities, waste, and the like in the skin are removed together with the cosmetic agent. Such a cosmetic agent is roughly classified into: a cosmetic agent which turns into a film-like state with time after application thereof, and a cosmetic agent which maintains the paste form over time.

The cosmetic agent which turns into a film-like state after the application can be easily removed from the skin by holding a portion thereof and peeling off the film. On the other hand, as a method of removing the cosmetic agent which maintains the paste form even after the application from the skin, it is general to wipe off the cosmetic agent with cotton or the like, or rinse off the cosmetic agent with warm water or the like. Recently, a method of removing the used cosmetic agent more easily than these general methods has been desired.

For example, Patent Document 1 proposes a method of using a cosmetic agent mixed with an iron powder and a remover provided with a magnet in the main body in combination. The use of this method enables the removal of a cosmetic agent applied to the skin after use by a magnetic force.

Patent Documents 2 and 3 disclose an example of cosmetic agents removable from the skin by magnetic attraction force. Iron powders, iron oxide and color-coated iron powders are disclosed as the magnetic powders contained in these cosmetic agents.

PRIOR ART DOCUMENT

Patent Document

Patent Document 1: JP 2004-187874 A
Patent Document 2: JP 2004-155720 A
Patent Document 3: JP 2005-239563 A

SUMMARY OF THE INVENTION

Problem to be Solved by the Invention

However, in some cases, a cosmetic agent containing a conventional magnetic powder is hard to be attracted and removed from the skin, and the magnetic powder unattracted by a remover is left on the skin surface. In such a case, a separate face washing, or the like, is required for removing the magnetic powder left on the skin, causing inconvenience to users.

When an iron powder is used as the magnetic powder, the iron powder is easily to be oxidized after mixed with a cosmetic agent, causing the magnetic properties and color tone easily to change. For this reason, the magnetic powder has a problem of causing a variation in performance. The magnetic powder also has a problem of difficulty in storing for a long time because the magnetic properties and color tone easily change as the iron powder oxidized. These problems cannot be satisfactorily solved even when the iron powder is coated as described in Patent Document 2.

Thus, the cosmetic agent to be removed from the skin by a magnetic attraction force still needs to be improved, and the optimal condition for the magnetic powder mixed with a cosmetic agent has not been found yet.

The present invention was accomplished in view of the above problems, and thus provides an optimal magnetic powder adapted to be included in a cosmetic agent and to be removable by a magnetic attraction force from the cosmetic agent applied to the skin.

Means for Solving the Problem

One aspect of the present invention is a magnetic powder adapted to be included in a cosmetic agent and to be removable from the skin by a magnetic attraction force from the cosmetic agent applied to the skin, wherein the magnetic powder comprises a ferromagnetic ferrite, the magnetic powder has a mean volume particle diameter being 50 to 75 μm as determined from a particle size distribution obtained by laser diffraction scattering method, the magnetic powder has a content of particles with a particle diameter of less than 37 μm being 15% by mass or less, and a content of particles with a particle diameter of 105 μm or more being 5% by mass or less.

Effects of the Invention

The magnetic powder comprises a ferromagnetic ferrite. Ferrites are oxidized in advance and not easily further oxidized after mixed with the cosmetic agent. Consequently, the cosmetic agent mixed with the magnetic powder is easy to control a variation in performance. The cosmetic agent also has little changes in effectiveness even when stored for a long time as the magnetic properties and color tone hardly change.

The magnetic powder further has the particle size distribution in the above specific range, by which, particularly, not only the mean volume particle diameter is controlled, but also both of the content of the large particles having a larger particle diameter than the above specific particle diameter and the content of the small particles having a particle diameter less than the above specific particle diameter are regulated. By specifically controlling the particle size distribution of magnetic powder, it can simultaneously optimize attraction of the magnetic powder in the cosmetic agent from the skin and smooth skin feel when the cosmetic agent touches the skin.

More specifically, in addition to controlling the mean volume particle diameter of the magnetic powder to 75 μm or less, the content of the large particles is further regulated to less than the above specific amount so that the magnetic powder can have a reduced roughness at the skin contact. As a result, the cosmetic agent including the magnetic powder provides a smooth skin touch.

Further, in addition to controlling the mean volume particle diameter of the magnetic powder to 50 μm or more, the content of the small particles is further regulated to less than the above specific amount, so that the magnetic attraction force working throughout the entire magnetic powder can be increased. As a result, a user can efficiently attract and remove the magnetic powder from the skin. Also, the magnetic powder hardly remains on the skin surface and thus obviates the necessity of a separate face washing for removing the magnetic powder, enhancing the convenience for users.

As described above, the magnetic powder has the optimal properties to be included in a cosmetic agent, which is attracted and removed from the skin.

BRIEF DESCRIPTION OF THE DRAWINGS

FIG. 1 is an explanatory drawing showing a usage of the cosmetic agent mixed with the magnetic powder in Example.

MODE FOR CARRYING OUT THE INVENTION

The magnetic powder is used as mixed in a flowable cosmetic agent such as a paste or a liquid. The cosmetic agent includes various beautifying components and is composed so that beauty effects such as nourishing the skin and lifting dirt components from the skin can be provided. The cosmetic agent may further be composed so that, in accordance with an intended beauty effect, the beautifying component remains at least partially on the skin surface when the magnetic powder is removed from the skin by a magnetic attraction force, or may also be composed so as to be substantially removed entirely from the skin surface with the magnetic powder.

In the magnetic powder, the mean volume particle diameter can be calculated in terms of 50% cumulative particle diameter (median diameter) obtained in the volume distribution mode in under-sieve representation of the particle size distribution obtained by the laser diffraction scattering method.

The content of the particles having a particle diameter less than 37 μm (hereinafter, in some cases, referred to as "small particle") can be measured, for example, in terms of the amount of particles passable through a standard sieve having a nominal dimension of 37 μm (400 mesh).

The content of the particles having a particle diameter of 105 μm or more (hereinafter, in some cases, referred to as "large particle") can be measured, for example, as an amount of particles not passable through a standard sieve having a nominal dimension of 105 μm (145 mesh).

When the mean volume particle diameter is less than 50 μm, the particle size distribution tends to have a high content of the particles having an excessively small particle diameter. The smaller the particle diameter is, the weaker the magnetic attraction force working on an individual particle is. Thus, when the magnetic powder contains a large amount of the particles having an excessively small particle diameter, a magnetic attraction force working throughout the entire magnetic powder tends to be weak and consequently the magnetic powder may not easily be attracted and removed from the skin.

However, it is still difficult to assure the reduction of a content of the particles having an excessively small particle diameter by simply controlling the mean volume particle diameter to 50 μm or more. For this reason, it is important to regulate a content of the small particles to 15% by mass or less as described above, in addition to controlling the mean volume particle diameter to 50 μm or more. When a content of the small particles is regulated to 15% by mass or less, the reduction of a content of the particles having an excessively small particle diameter can be assured.

On the other hand, when the mean volume particle diameter exceeds 75 μm, the particle size distribution tends to have a high content of the particles having an excessively large particle diameter. Consequently, in this case, a sense of use may become poor such as poor skin feel of the cosmetic agent mixed with the magnetic powder.

However, it is still difficult to assure the reduction of a content of the particles having an excessively large particle diameter by simply controlling the mean volume particle diameter to 75 μm or less. For this reason, it is important to regulate a content of the large particles to 5% by mass or less as described above, in addition to controlling the mean volume particle diameter of 75 μm or less. When a content of the large particles is regulated to 5% by mass or less, the reduction of a content of the particles having an excessively large particle diameter can be assured.

As described above, the optimal particle size distribution having a high content of suitable size particles can be realized by, in addition to controlling the mean volume particle diameter of the magnetic powder to the above specific range, further regulating both of the content of the small particles and the content of the large particles. As a result, both properties of the performance of being attracted and removed and the skin feel of the magnetic powder can be optimized.

The ferrite composing the magnetic powder includes spinel-type ferrite, magnetoplumbite-type ferrite, garnet-typeferrite, perovskite-type ferrite or the like. The magnetic powder may include one kind of the compound selected from the ferrite compounds, or may include two or more kinds of the compounds.

The ferrite used in the magnetic powder is preferably a soft ferrite, which is high in saturation magnetization and low in both residual magnetization and coercive force. Specific examples of the soft ferrite include spinel type ferrites having the composition represented by $(MO)_x(Fe_2O_3)_y$ (provided that x+y=100 mol % and M is one or more elements selected from the metal elements such as Fe, Mn, Mg, Sr, Ca, Ba, Cu, Zn, Ni, Li, and Co). Further, of the spinel type ferrites, it is more preferred to use the ferrites having a high saturation magnetization. It is further preferred, for enhancing the saturation magnetization, to contain as the main component magnetite ($Fe_3O_4$) wherein M in the above general formula is replaced with Fe.

The magnetic powder preferably has a saturation magnetization of 80 $Am^2/kg$ or more. In this case, the magnetization of the magnetic powder can be increased and accordingly the magnetic attraction force working on the magnetic powder can be more increased. As a result, the magnetic powder can be more efficiently attracted and removed from the skin.

Further, the magnetic powder has the supernatant liquid, which is obtained by dispersing the magnetic powder in methanol, having a transmittance at a wavelength of 474 nm of 90% or more. The transmittance of the supernatant liquid is the index value for the content of the particles having an extremely small particle diameter, and it shows that the higher the transmittance is, the lower the content of such a particle is. When a transmittance of the supernatant liquid is 90% or more, the magnetic powder has a low content of such a particle. As a result, the magnetic powder can be more efficiently attracted and removed from the skin.

Furthermore, the magnetic powder preferably has an apparent density of 1.95 to 2.65 $g/cm^3$.

The apparent density of the magnetic powder is the index value for the average shape of the particles composing the magnetic powder, and it shows that the higher the apparent density is, the more the average shape of the particles approaches to true spherical. More specifically, the magnetic powder having a high apparent density is likely to contain a large amount of substantially spherical particles with comparatively small unevenness. On the other hand, the magnetic powder having a low apparent density is likely to contain a large amount of non-spherical particles, such as ellipsoid or lumps, with comparatively large unevenness.

Further, the magnetic powder having a high apparent density is likely to contain particles each having a larger mass than the magnetic powder having a low apparent density. Thus, the magnetic force working throughout the entire magnetic powder is likely to be strong. This is presumably caused by that a volume of the space present inside the particle reduces when an apparent density becomes higher, or the like.

When an apparent density of the magnetic powder exceeds 2.65 g/cm$^3$, a content of the particles having an excessively large mass is likely to be high. For this reason, the magnetic powder is hard to be homogeneously dispersed as mixed in the cosmetic agent, and in some cases the magnetic powder may settle during storage or the like.

On the other hand, when an apparent density is less than 1.95 g/cm$^3$, the unevenness of the particle is likely to be excessively large. Accordingly, the viscosity of the cosmetic agent may be increased, and it may be considered that the cosmetic agent is not easily applicable to the skin in some cases.

When an apparent density is less than 1.95 g/cm$^3$, there are two possibilities that the crystal growth of the particle may be insufficient, and the crystal growth of the particle may excessively proceed. When the crystal growth of the particle is insufficient, the unevenness may be excessively large as described above, and further the strength of the particle may be deteriorated and, in some cases, breakage and chipping of particles during use may be considered. As described above, such an excessively large unevenness and the occurrence of breakage or chipping of particles are not preferable due to causing poor skin feel or the deterioration of magnetic attraction force working on the particles.

Further, when the crystal growth of particle excessively proceeds, the particles are too easily fused with each other and such a fusion may cause excessively large unevenness of particles as described above. Furthermore, with this, when the fused particles are crushed, the unevenness of the particles occurred by the crushing may become excessively distinctive. Consequently, in this case, the sense of use may become poor such as deteriorated spreadability of cosmetic agent when applied to the skin or poor skin feel in application.

The magnetic powder preferably has a specific surface area of 200 to 450 cm$^2$/g when measured using an air permeability method. The specific surface area of the magnetic powder is the index for the micro structure such as pores formed on the surface of particles, and it shows that the larger the value of a specific surface area is, the more pores and the like are formed.

When the specific surface area of the magnetic powder is less than 200 cm$^2$/g, the micro structure of pores and the like may not be formed sufficiently. As a result, the particles may hold a less amount of the cosmetic agent on the surface and not be easily dispersed in the cosmetic agent. On the other hand, when the specific surface area of the magnetic powder exceeds 450 cm$^2$/g, the micro structure may be formed excessively and the beautifying components may deeply enter into the micro structure. For this reason, the amount of the beautifying components working directly to the skin may be reduced, causing the deterioration of the beauty effects.

The magnetic powder may also be composed so as to exhibit other functions using techniques such as bonding the beautifying components to the surface, or coating the surface with the components. Examples of the function imparted to the magnetic powder include improving the dispersibility of the magnetic powder using a surfactant or the like, and attracting and removing the skin sebum together with the magnetic powder using a sebum adsorption resin component or the like.

Thus, when the surface of the magnetic powder is modified using a surface modifier such as a coating agent, it is preferred that the magnetic powder contains particles imparted with suitably large unevenness. The particle having suitably large unevenness has a larger specific surface area than the particle having small unevenness, thereby easily retaining a surface modifier. Thus, the magnetic powder containing such a particle in a large amount is likely to attain surface modification effects rendered by a surface modifier. On the other hand, in the case where a large amount of the particle having small unevenness such as substantially spherical shape is contained, a surface modifier does not easily adhere to an individual particle and surface modification effects may not be easily exerted.

For easy achievement of the effect of a surface modifier, the apparent density is preferably 1.95 to 2.65 g/cm$^3$, and the specific surface area is preferably 200 to 450 cm$^2$/g when measured using an air permeability method. The effect of a surface modifier becomes easily achievable when either of the values of the apparent density or the specific surface area is within the above specific ranges, and the effect of a surface modifier becomes much easily achievable when both of the values satisfy the above specific ranges.

Note that the magnetic powder contains, other than ferrites, inevitable impurities derived from raw materials, production process, and the like. Examples of the inevitable impurities include lead and arsenic, but the contents of these impurities are usually regulated to lead: 40 ppm or less, and arsenic: 10 ppm or less.

Next, the method for producing the magnetic powder is described. For the method for producing the magnetic powder, a conventionally known method can be employed. An embodiment of the method for producing the magnetic powder includes a method in which predetermined raw materials and auxiliary materials are grinded, mixed and subsequently granulated, and the obtained granulated product is fired and further crushed, followed by classifying process.

For the raw materials for the magnetic powder, natural ores containing ferrites, metal compound industrially produced, and the like can be used.

For example, when magnetite (Fe$_3$O$_4$) is used as the ferrite, a natural ore containing magnetite can be used as the raw material. Alternatively, magnetite obtained by reducing hematite (Fe$_2$O$_3$) industrially produced may be used as the raw material. When a method for reducing hematite is used, the purity and composition of the obtained magnetite can be easily adjusted. As a result, the quality of the magnetic powder can be easily stabilized.

Hematite is reduced to magnetite, for example, by heating while co-existing with a carbon component. This reaction theoretically follows the reaction formula below.

$$6Fe_2O_3 + C \rightarrow 4Fe_3O_4 + CO_2$$

Accordingly, for the complete reduction of hematite to magnetite, at least 1.25 parts of mass of carbon relative to 100 parts of mass of hematite is required. In the actual production conditions, the blending according to the above reaction formula may sometimes fail to completely reduce hematite, and it is thus preferred to blend carbon more than 1.25 parts by mass.

When a ferrite other than magnetite is used, a method can be employed in which hematite industrially produced and a metal compound selected in accordance with the desired property are mixed and subsequently reacted at the time of firing or the like. Specifically, when Mn ferrite is produced, a manganese compound such as manganese carbonate or manganomanganic oxide or the like can be used as the above metal compound. Further, when Mg ferrite is produced, a magnesium compound such as magnesium hydroxide or magnesium oxide can be used.

The method for preparing a granulated product from grinded and mixed raw materials and the like may be either a dry method or a wet method. When the wet method is employed, for example, raw materials and water are mixed, the mixture is grinded using a ball mill or the like, and subsequently the viscosity is adjusted by adding, as necessary, a dispersant, a binder or the like to obtain a slurry mixture. Then, the granulation of the mixture can be carried out using a spray dryer. In this case, for the binder, polyvinyl alcohol and polyvinylpyrrolidone are preferably used.

The firing of the granulated product is typically carried out by heating at a temperature of 1100 to 1400° C. for 1 to 24 hours. The furnace used for the firing can be those already known such as a rotary electric furnace, batch-type electric furnace, or tunnel electric furnace. Further, the atmosphere during the firing can be suitably selected in consideration with the target oxidation degree and magnetic property.

The classification method of the fired product, which was obtained by the firing and crushed, can be a known method such as air classification, mesh filtration, sedimentation or the like. In case of the performing dry collection, cyclone or the like can be used for the collection. Alternatively, more than one of these classification methods can be used in combination. When the classification process is carried out using these methods, the particle size distribution of the magnetic powder can be adjusted to a desired distribution.

Further, the magnetic separation may be carried out as necessary before or after the classification process. Particles having a low magnetic susceptibility can be removed by performing the magnetic separation.

EXAMPLES

Examples of the above magnetic powder are described below. The magnetic powder of the present Example is composed of a ferromagnetic ferrite. Further, as shown in Table 1, the magnetic powder of the present Example has a mean volume particle diameter of 50 to 75 μm when determined from a particle size distribution obtained by a laser diffraction scattering method, a content of the particles with a particle diameter of less than 37 μm (small particle) of 15% by mass or less, and a content of the particles with a particle diameter of 105 μm or more (large particle) of 5% by mass or less.

The magnetic powder is used as mixed with a paste cosmetic agent 1 to be applied to the skin, as shown in FIG. 1. The cosmetic agent 1 of the present Example is composed so that the magnetic powder is removed from the skin by a magnetic attraction force generated at a magnetic force generating surface 20 of a remover 2, and consequently the beautifying components remain on the skin surface.

In the present Example, various magnetic powders to be included in cosmetic agents (Samples No. 1 to No. 14) shown in Table 1 were produced.

<Method for Producing a Magnetic Powder Containing Magnetite as the Main Component>

Water was added to the powder obtained by grinding hematite ($Fe_2O_3$) so that a solid content was 55% by mass to prepare a slurry. Next, 1% by mass of polyvinyl alcohol, 0.9% by mass of carbon black and 0.5% by mass of polycarboxylate, relative to the solid content of the obtained slurry, were added to the slurry, and the resulting slurry was stirred using an attritor for 1 hour. Subsequently, the slurry was granulated into spherical using a spray drier and the particle size of the obtained granulated product was adjusted using a gyroshifter.

Next, the spherical granulated product having the adjusted particle size was heated at 1320° C. for 3 hours to reduce a raw material hematite, thereby obtaining a fired product having magnetite as the main component. Note that the heating of the granulated product was carried out using a tunnel electric furnace under a nitrogen atmosphere.

The obtained fired product was crushed and subsequently subjected to the classification process using a gyroshifter and an air classifier in combination to adjust the particle size distribution. Subsequently, the magnetic separation was carried out to select the particles having a high magnetic susceptibility, thereby obtaining a magnetic powder having magnetite as the main component (Sample No. 1).

Further, Samples No. 3 to No. 12 were obtained by suitably changing the amount of carbon black added, heating condition and classification condition from the production method of Sample No. 1.

<Method for Producing a Magnetic Powder Containing Mn Ferrite as the Main Component>

Hematite and manganomanganic oxide were weighed to be MnO: 20 mol % and $Fe_2O_3$: 80 mol % and grinded for 1 hour using a wet media mill to obtain a slurry. The obtained slurry was dried using a spray drier to obtain a spherical granulated product. Next, the particle size of the obtained granulated product was adjusted using a gyroshifter and the granulated product was preliminarily fired by heating at 950° C. for 2 hours.

Subsequently, water was added to the preliminarily fired granulated product so that a solid content was 55% by mass, and grinding and mixing were carried out for 1 hour using an attritor to prepare a slurry. Further, 2% by mass of polyvinyl alcohol relative to the solid content of the obtained slurry and an appropriate amount of a dispersant were added. Subsequently, the slurry was granulated into spherical using a spray drier and the particle size was adjusted using a gyroshifter.

Next, the spherical granulated product having the adjusted particle size was heated at 1310° C. for 3 hours to allow hematite and manganomanganic oxide to react, thereby obtaining a fired product having Mn ferrite as the main component. Note that the heating of the granulated product was carried out using a tunnel electric furnace under a nitrogen atmosphere.

The obtained fired product was crushed and subsequently subjected to the classification process using a gyroshifter and an air classifier in combination to adjust the particle size distribution. Subsequently, the magnetic separation was carried out to select the particles having a high magnetic susceptibility, thereby obtaining a magnetic powder having Mn ferrite as the main component (Samples No. 2 and No. 14).

For Sample No. 13, a commercial spherical iron powder having a mean volume particle diameter of about 80 μm was used.

Using each of the samples obtained by the method described above, each of the properties was evaluated by the following methods.

<Mean Volume Particle Diameter>

An aqueous solution of 0.2% sodium hexametaphosphate was added to the sample, subsequently ultrasonic treatment was carried out for 1 minute using a ultrasonic homogenizer (manufactured by Ultrasonic Engineering Co., Ltd., UH-3C) to prepare a dispersion liquid of the magnetic powder. The dispersion liquid was introduced to a Microtrac Particle Size Analyzer (Nikkiso Co., Ltd., Model 9320-X100) and measured under the conditions of a refractive index of 1.81, a temperature of 25±5° C. and a humidity of 55±15% to obtain a particle size distribution by a laser diffraction scattering method. Based on the obtained particle size distribution, a 50% cumulative particle diameter in the volume distribution mode in under-sieve representation was calculated to use as the mean volume particle diameter (median diameter).

<Content of the Small Particle and Content of the Large Particle>

The classification of the samples was carried out using a standard sieve defined in JIS Z 8801 by the method according to JIS H 2601. By this procedure, the content of particles passed through a standard sieve having a nominal dimension of 37 μm (400 mesh) (the small particle) and the content of particles not passed through a standard sieve having a nominal dimension of 105 μm (145 mesh) (the large particle) were measured.

<Apparent Density>

The measurement was carried out by the following method according to Metallic powders—Determination of apparent density defined in JIS Z 2504. A measurement apparatus for the apparent density used was equipped with a funnel having an orifice with a pore diameter of $2.5^{+0.2/0}$ mm, a cup, a funnel supporter, a supporting rod and a supporting stand. First, at least 150 g of the sample was poured into the funnel, and the sample flowing out of the funnel was directly poured into the cup mounted at the lower part of the funnel. After the cup was filled with the sample, the pouring of the sample was immediately stopped at the time that the sample started overflowing.

Next, a flat spatula made from a non-magnetic material was horizontally moved along the opening surface of the cup to skim off the arising sample from the cup. Subsequently, the cup was lightly tapped on the side to stabilize the sample, the sample attached to the side of the cup was wiped off, and the weight of the sample inside the cup was weighed using a balance scale having a measuring maximum weight of 200 g and a reciprocal sensitivity of 50 mg. The obtained weight value was multiplied by 0.04 and the resulting numerical value was rounded off to the second decimal place using Guide to the rounding of numbers defined in JIS Z 8401, thereby obtaining a value to be the apparent density (g/cm$^3$).

<Saturation Magnetization, Residual Magnetization and Coercive Force>

Using an integral type B-H tracer (manufactured by Riken Denshi Co., Ltd., BHU-60 model), the measurement was carried out by the following procedure. First, an H coil for measuring magnetic field and a 4πI coil for measuring magnetization are placed in between electromagnets, and the sample was placed in the 4πI coil. Next, outputs of the H coil and the 4πI coil when the magnetic field H was changed by changing the current of the electromagnets are each integrated, and a hysteresis loop is drawn on a recording chart with the H output as the X-axis and the 4πI coil output as the Y-axis. Saturation magnetization, residual magnetization and coercive force were read from the hysteresis loop. The measurements of saturation magnetization, residual magnetization and coercive force were carried out by packing about 1 g of the sample in a cell having an inner diameter of 7 mmφ±0.02 mm and a height of 10 mm±0.1 mm, under the conditions of 4πI coil: winding number of 30 and an applied magnet field: 3000 oersted.

<Supernatant Transmittance>

15 g of the sample was weighed and placed in a 50 ml sample bottle. 20 ml of methanol was added to this sample bottle, the bottle was closed with a lid, and substantially stirred at 150 rpm for 20 minutes using a rotary stirrer. After completing stirring, a magnet was allowed to contact the bottom of the sample bottle to attract the sample, and, with this condition, the sample bottle was mixed by shaking 3 times with hands. Subsequently, 3 ml of the supernatant liquid of the sample bottle was collected and the transmittance at a wavelength of 474 nm of the supernatant liquid was measured using a visible spectrophotometer (manufactured by Ogawa Seiki Co., Ltd., Model 6100). Note that methanol was used as the blank sample in the transmittance measurement.

<Specific Surface Area>

After a plastic sample tube was packed with the sample, the specific surface area was measured by the air permeability method using a powder specific surface area measuring device (manufactured by Shimadzu Corporation, Model SS-100). More specific method for packing the sample and measurement procedure are as follows.

(1) Sample Packing

A sieve plate was placed in a plastic sample tube, and the sample tube was mounted on a tapping stand of a powder tester (manufactured by Hosokawa Micron Corporation) with a sheet of filter paper further placed on the tube. Next, the sample was poured up to about ⅓ of the sample tube, and the powder tester was turned on to tap the sample tube for 60 seconds. After tapping, the sample was additionally poured up to about ⅔ of the sample tube, and the powder tester was restarted to tap the sample tube for 60 seconds. Subsequently, the sample was additionally poured until the sample tube was full, and the powder tester was turned on to tap the sample tube for 60 seconds. After completing the third tapping, the excessive sample attached to the sample tube was removed using a brush or a wiper, thereby completing the sample packing.

(2) Measurement of Specific Surface Area

Vaseline was applied to the lower part of the sample tube, and a measurement tube was connected to this part, followed by pouring pure water to the measurement tube. Next, a discharge cock at the lower part of the measuring device was opened and the pure water was allowed to flow out of the measurement tube and the time t required for a water level in the measurement tube to lower to a volume equivalent to 20 cc. The Kozeny-Carman formula (see the following formula (1)) was substituted with the thus obtained time t (sec) required for 20 cc of air to permeate the sample packed bed and the weight W (g) of the sample packed in the sample tube to determine the specific surface area Sw of the sample.

[Expression 1]

$$Sw = \frac{14}{\rho} \sqrt{\frac{\Delta PAt}{\eta LQ} \cdot \frac{\varepsilon^3}{(1-\varepsilon)^2}} \quad \text{(formula 1)}$$

ε in the formula (1) herein is a void fraction of the sample packed bed determined by the following formula (2).

[Expression 2]

$$\varepsilon = 1 - \frac{W}{\rho A L} \quad \text{(formula 2)}$$

Note that other symbols in the above formula (1) and formula (2) mean as follows.
Specific surface area of sample: Sw ($cm^2/g$)
Density of sample: $\rho$ ($g/cm^3$)
Viscosity coefficient of air: $\eta$ (g/cm·sec)
Thickness of the sample packed bed: L (cm)
Volume of air permeated the sample packed bed: Q (cc)
Pressure difference between both ends of the sample packed bed: $\Delta P$ ($g/cm^2$)
Cross-section area of the sample packed bed: A ($cm^2$)

Table 1 showed each of the properties of the magnetic powder evaluated by the above methods.

sured value was shown in the column of "attraction distance" in Table 2. It shows that the larger the value shown in Table 2 is, the easier the removal of the magnetic powder by attraction is. Note that the neodymium magnet built in the test head was cylindrically shaped and had a diameter of 25 mm and a height of about 8 mm, and had a surface inductive flux of 266 mT in terms of the magnet alone. The neodymium magnet was used with a disk-shaped yoke piece having a thickness of 2 mm disposed at the end facing the top of the neodymium magnet.

<Skin Feel>

The skin feel when the cosmetic agent was applied to the back of a hand was evaluated and the results were shown in Table 2.

Note that the meaning of each of the symbols shown in Table 2 is as follows.
A: No rough feel was noted.
B: Almost no rough feel was noted.

TABLE 1

| | | Particle size distribution | | | Magnetic property | | | Shape of particle | |
|---|---|---|---|---|---|---|---|---|---|
| Sample No. | Main component | Mean volume particle diameter (μm) | Content of small particle (% by mass) | Content of large particle (% by mass) | Transmittance of supernatant liquid (%) | Saturation magnetization ($Am^2/kg$) | Residual magnetization ($Am^2/kg$) | Coercive force (Oe) | Apparent density ($g/cm^3$) | Specific surface area ($cm^2/g$) |
| 1 | Magnetite | 58.0 | 7.6 | 0.0 | 99.9 | 85 | 2 | 12 | 2.24 | 336 |
| 2 | Mn ferrite | 61.0 | 3.2 | 0.0 | 99.9 | 94 | 1 | 10 | 2.50 | 219 |
| 3 | Magnetite | 50.5 | 14.7 | 0.0 | 99.9 | 84 | 3 | 18 | 2.27 | 398 |
| 4 | Magnetite | 71.6 | 0.1 | 0.4 | 99.8 | 84 | 3 | 18 | 2.10 | 317 |
| 5 | Magnetite | 59.9 | 13.4 | 4.8 | 99.9 | 85 | 2 | 12 | 2.24 | 368 |
| 6 | Magnetite | 60.2 | 3.8 | 2.2 | 99.8 | 81 | 3 | 18 | 2.30 | 322 |
| 7 | Magnetite | 62.0 | 3.5 | 0.0 | 99.9 | 89 | 1 | 10 | 2.63 | 200 |
| 8 | Magnetite | 56.4 | 6.0 | 0.1 | 99.1 | 85 | 1 | 12 | 1.98 | 421 |
| 9 | Magnetite | 61.1 | 19.2 | 6.5 | 100 | 85 | 2 | 12 | 2.23 | 387 |
| 10 | Magnetite | 39.5 | 44.5 | 0.0 | 100 | 85 | 3 | 18 | 2.14 | 494 |
| 11 | Magnetite | 79.1 | 5.0 | 20.8 | 79.1 | 76 | 4 | 30 | 2.80 | 196 |
| 12 | Magnetite | 117.9 | 0.0 | 62.6 | 98.8 | 79 | 3 | 24 | 2.75 | 145 |
| 13 | Iron | 99.5 | 0.0 | 37.7 | 90.6 | 180 | 2 | 13 | 4.38 | 89 |
| 14 | Mn ferrite | 106.7 | 0.0 | 46.0 | 99.7 | 94 | 1 | 10 | 2.70 | 142 |

Next, the properties of the cosmetic agent mixed with the magnetic powder were evaluated by the following methods.

Note that, for the above property evaluation, the cosmetic agent having the following composition was used.
Magnetic powder 60.0% by mass
Glycerol 20.0% by mass
Methyl paraben 0.38% by mass
Decamethylcyclopentasiloxane 1.3% by mass
Trioctyl glyceryl 3.8% by mass
Cetyl 2-ethylhexanoate 3.8% by mass
Bentonite 0.19% by mass
Polyoxyethylene-methyl polysiloxane copolymer 2.25% by mass
Polyglyceryl monolaurate 0.25% by mass
Sodium polyacrylate 0.01% by mass
Sodium hydroxide 0.03% by mass
Sodium ascorbyl phosphate 0.13% by mass
Flavor 0.13% by mass
Water Balance <Attraction Removability>

The cosmetic agent mixed with the magnetic powder was applied to a flat plate mounted on a level surface. A test head having a neodymium magnet built-in was moved closer from above to the applied cosmetic agent, the height from the flat plate to the test head at the time of attracting the magnet powder to the test head was measured. The mea- C: Rough feel was noted but applicable and spreadable.
D: Rough feel was noted and not applicable or spreadable.

<Color Tone>

Using a color difference meter (manufactured by Nippon Denshoku Industries Co., Ltd., Model type "ZE 2000"), the L value (lightness), a value (green to red chromaticity), and b value (blue to yellow chromaticity) of the magnetic powder were measured and each of the measured values was shown in Table 2. Note that, for the measurement, 5 g of the magnetic powder was used.

TABLE 2

| | Property evaluation | | | | | |
|---|---|---|---|---|---|---|
| Sample No. | Attraction distance (mm) | Skin feel | Color tone L | a | b | Overall Result |
| 1 | 14 | A | 19.50 | 0.30 | 0.80 | A |
| 2 | 15 | B | 19.90 | −0.50 | 1.90 | A |
| 3 | 14 | B | 20.60 | 0.30 | 0.80 | B |
| 4 | 14 | B | 20.00 | 0.20 | 0.90 | B |
| 5 | 14 | B | 19.20 | 0.18 | 0.78 | B |
| 6 | 15 | B | 19.90 | 0.30 | 0.80 | B |
| 7 | 14 | B | 20.60 | −0.50 | 1.90 | B |
| 8 | 15 | B | 19.50 | 0.20 | 1.10 | B |
| 9 | 14 | C | 20.10 | 0.30 | 0.80 | C |

TABLE 2-continued

| | Property evaluation | | | | | |
|---|---|---|---|---|---|---|
| Sample No. | Attraction distance (mm) | Skin feel | Color tone L | a | b | Overall Result |
| 10 | 14 | D | 20.50 | 0.30 | 0.80 | D |
| 11 | 13 | D | 22.50 | −1.40 | −0.30 | D |
| 12 | 14 | D | 22.40 | −1.20 | −1.10 | D |
| 13 | 17 | D | 23.90 | 0.60 | 3.40 | D |
| 14 | 13 | D | 20.60 | −0.30 | 1.40 | D |

As revealed in Table 2, the samples having the mean volume particle diameter, the content of the large particles and the content of the small particles controlled to the above specific ranges were outstanding in all of the attraction removability, skin feel, and color tone, and thus consequently preferable to be a cosmetic agent.

The invention claimed is:

1. A magnetic powder, comprising:
a granulated powder of ferromagnetic ferrite,
wherein the granulated powder has:
a mean volume particle diameter of 50 to 75 µm as determined from a particle size distribution obtained by a laser diffraction scattering method;
a content of particles with a particle diameter of less than 37 µm of 15% by mass or less;
a content of particles with a particle diameter of 105 µm or more of 5% by mass or less;
a saturation magnetization of 80 $Am^2/kg$ or more;
a transmittance of 90% or more at a wavelength of 474 nm of a supernatant liquid obtained by dispersing the magnetic powder in methanol;
an apparent density of 1.95 to 2.65 $g/cm^3$; and
a specific surface area of 200 to 450 $cm^2/g$ as measured using an air permeability method.

2. A cosmetic agent applied to skin, comprising:
the magnetic powder of claim 1,
wherein the magnetic powder is removable by a magnetic attraction force from the cosmetic agent.

3. The magnetic powder of claim 1, obtained by a method comprising:
grinding and mixing at least one ferromagnetic ferrite raw material and at least one auxiliary material to obtain a grounded mixture,
granulating the grounded mixture to obtain a granulated product,
firing the granulated product to obtain a fired product,
crushing the fired product to obtain a crushed product, and
classifying the crushed product.

4. The magnetic powder of claim 3, wherein the method further comprises:
magnetically separating the crushed product before or after said classifying.

5. The magnetic powder of claim 1, which is modified by a surface modifier.

6. The magnetic powder of claim 5, wherein the surface modifier is a coating agent.

* * * * *